(12) United States Patent
Yuds et al.

(10) Patent No.: US 12,397,145 B2
(45) Date of Patent: Aug. 26, 2025

(54) SELF-SEALING FLUID CONNECTORS

(71) Applicant: Fresenius Medical Care Holdings, Inc., Waltham, MA (US)

(72) Inventors: David Yuds, Hudson, NH (US); Eric Bergman, Newton, MA (US); Jonathan Leclerc, Northborough, MA (US); Jessica Steuber, Berlin, MA (US); Areeba Zakir, Cambridge, MA (US); Laura Chang, Cambridge, MA (US); Diego Suarez del Real Pena, Waltham, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 464 days.

(21) Appl. No.: 17/977,785

(22) Filed: Oct. 31, 2022

(65) Prior Publication Data

US 2023/0149612 A1    May 18, 2023

Related U.S. Application Data

(60) Provisional application No. 63/279,743, filed on Nov. 16, 2021.

(51) Int. Cl.
  *A61M 39/10*    (2006.01)
  *A61M 1/16*    (2006.01)
  (Continued)

(52) U.S. Cl.
  CPC ...... *A61M 39/1011* (2013.01); *A61M 1/1654* (2013.01); *A61M 1/28* (2013.01);
  (Continued)

(58) Field of Classification Search
  CPC ...... A61M 1/1654; A61M 1/28; A61M 1/284; A61M 39/1011; A61M 39/286;
  (Continued)

(56) References Cited

U.S. PATENT DOCUMENTS 5,438,510 A    8/1995   Bryant et al.

FOREIGN PATENT DOCUMENTS

WO    WO 1998/002206    1/1998

OTHER PUBLICATIONS

Karidis, "How the Healthcare Industry is Addressing the Fast-growing Medical Waste Problem," May 17, 2018, retrieved on Jan. 12, 2023, retrieved from URL <https://www.waste360.com/medical-waste/how-healthcare-industry-addressing-fast-growing-medical-waste-problem>, 9 pages.

(Continued)

*Primary Examiner* — John Kim
(74) *Attorney, Agent, or Firm* — Fish & Richardson P.C.

(57) ABSTRACT

The present teachings may generally include a first fluid connector that includes a first body having a first central cavity that defines a first fluid pathway and a first seal within the first central cavity. The first seal includes a pair of first interfacing elements positioned adjacent one another at a distal end of the first seal and a first opening configured to remain sealed closed when the first interfacing elements are adjacent, and the first opening opens when the first interfacing elements are separated. The first connector is configured to fluidly connect to a second connector by engaging the first interfacing elements and with a pair of second interfacing elements of the second connector, thereby causing both pairs of first and second interfacing elements to separate causing the opening of first opening and second opening.

14 Claims, 9 Drawing Sheets

(51) Int. Cl.
    *A61M 1/28*     (2006.01)
    *A61M 39/28*    (2006.01)
    *A61M 39/26*    (2006.01)

(52) U.S. Cl.
    CPC ..... *A61M 1/284* (2014.02); *A61M 2039/1016* (2013.01); *A61M 2039/1027* (2013.01); *A61M 2039/1072* (2013.01); *A61M 2039/263* (2013.01); *A61M 39/286* (2013.01); *A61M 2205/12* (2013.01); *A61M 2205/6081* (2013.01)

(58) Field of Classification Search
    CPC ...... A61M 2205/12; A61M 2205/6081; A61M 2039/1016; A61M 2039/1027; A61M 2039/1072; A61M 2039/263
    See application file for complete search history.

(56) References Cited

OTHER PUBLICATIONS

International Preliminary Report on Patentability in International Appln. No. PCT/US2022/048418, mailed May 30, 2024, 9 pages.
International Search Report and Written Opinion in International Appln. No. PCT/US2022/048418, mailed Apr. 24, 2023, 16 pages.

SELF-SEALING FLUID CONNECTORS

CLAIM OF PRIORITY

This application claims priority under 35 USC § 119(e) to U.S. Patent Application Ser. No. 63/279,743, filed on Nov. 16, 2021, the entire contents of which are hereby incorporated by reference.

FIELD

The present disclosure generally relates to self-sealing fluid connectors for fluid lines, for example, self-sealing fluid connectors for medical applications including dialysis (e.g., peritoneal dialysis or hemodialysis).

BACKGROUND

Dialysis is a treatment used to support a patient, whose renal function has decreased to a point where the kidneys no longer sufficiently function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

Figure 1:
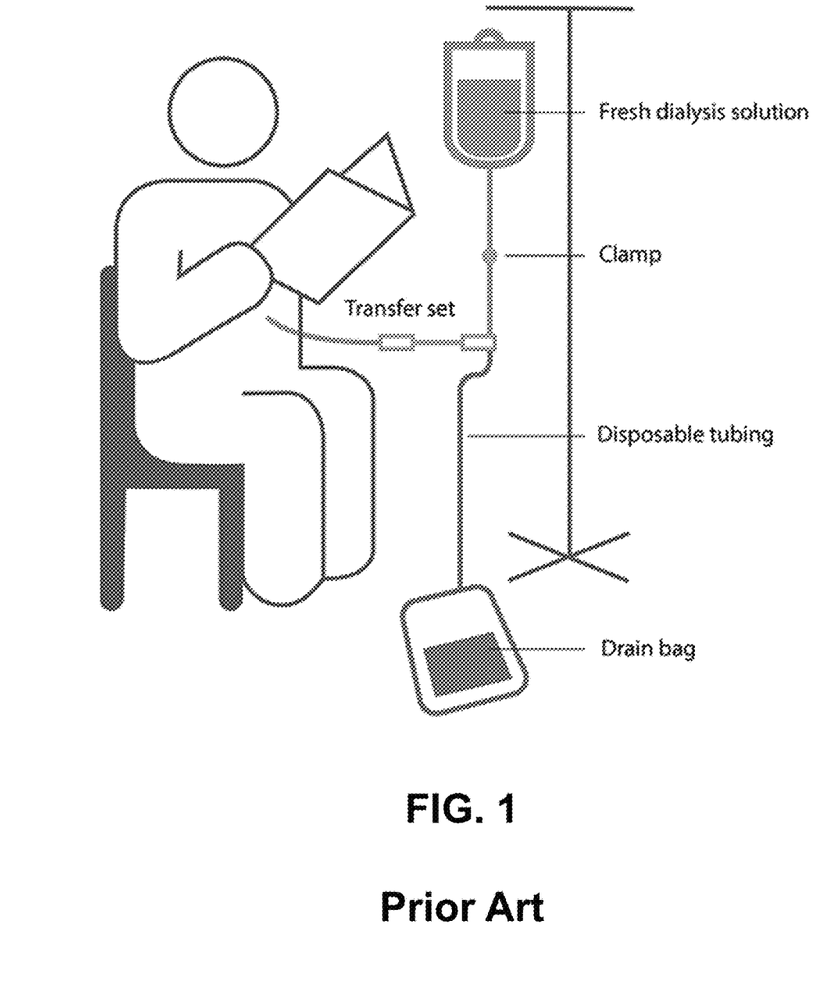
FIG. 1 illustrates a schematic of a continuous ambulatory peritoneal dialysis (CAPD) arrangement.

During peritoneal dialysis ("PD"), a patient's peritoneal cavity is periodically infused with sterile aqueous solution, referred to as PD solution or dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood. There are two types of peritoneal dialysis therapy, continuous ambulatory peritoneal dialysis (CAPD) and automated peritoneal dialysis (APD). CAPD is performed manually and done while a person goes about their normal activities. FIG. 1 illustrates a schematic of the arrangement for a CAPD exchange. APD differs from CAPD in that a cycler 20 (see e.g., FIG. 2) delivers and then drains the cleansing fluid automatically.

PD patients are required to open and close line clamps at various times during their therapy, for example, when they set up the system for treatment and when they disconnect following treatment. Some of the routine types of clamp interactions for a PD patient include: clamping lines not connected to solution bags, clamping the drain bag/line to drain when disconnecting, clamping each of the lines coming out of the cassette when disposing of it (e.g., drain line, four solution bag lines, heater bag line, and patient line), and clamping solution supply bags when disposing of them. As demonstrated by the APD cassette 30 shown in FIG. 3, there can be numerous fluid lines and clamps a PD patient must handle and keep track of to complete a PD treatment. It can be a challenge for a PD patient to keep track of all the clamps and their status (open/closed) and patients with dexterity issues can have trouble physically opening and closing these clamps. Failure to open and close the clamps as required can result in frustration, confusion, spills, contamination, and treatment delays. Additionally, if a clamp that is not normally closed is closed at the wrong time in the patient treatment workflow, patients can have a difficult time tracking down the source of the error.

There remains a need for simplifying PD treatments and the challenge all the clamps present for a PD patient. Furthermore, the sheer number of disposable clamps per treatment also contributes cost to each treatment and is part of a growing concern for medical waste. Exemplary embodiments of the present disclosure aim to remedy the challenges the plethora of clamps present.

SUMMARY

Figure 3:
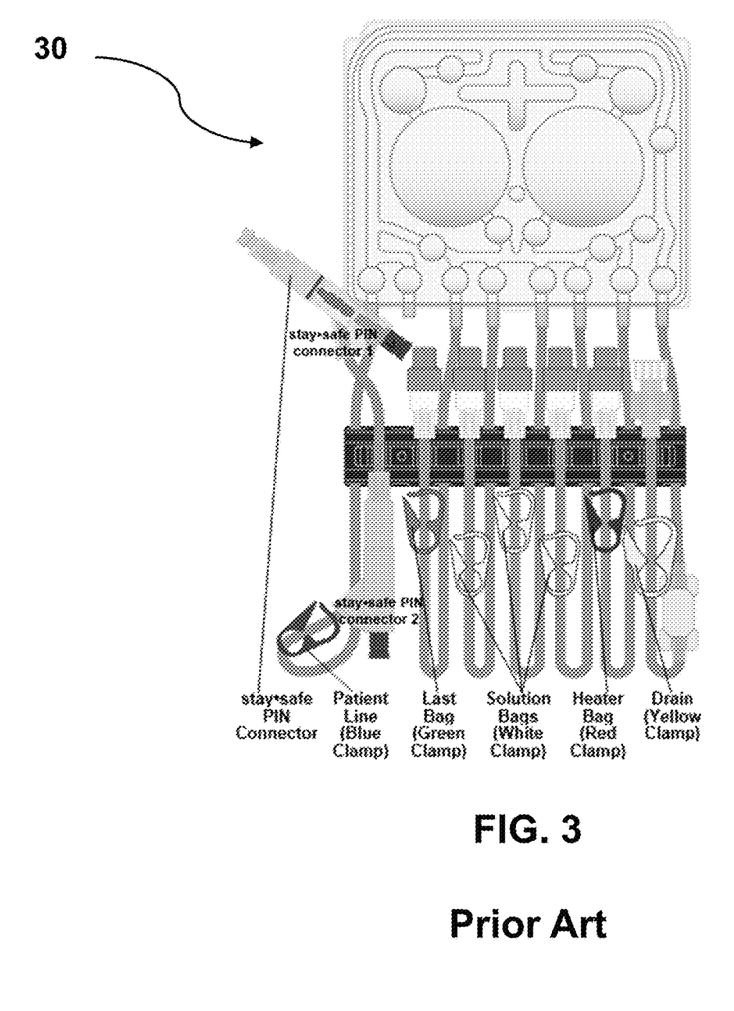
FIG. 3 illustrates a cassette and fluid lines, clamps, and connectors for use with an APD unit as shown in FIG. 2.

The present disclosure generally includes self-sealing fluid connectors sets configured to eliminate the need for clamps and can be functional replacements for the luer connectors (e.g., as shown in FIG. 3), commonly used for connecting two medical fluid lines. The self-seal sealing fluid connector sets can have a first connector and second connector, each connector being configured to be disposed at an end of a fluid line. Each connector is configured to remain sealed until the first connector and second connector are coupled (releasably) which automatically causes the fluid pathway of each connector to open thereby becoming fluidly coupled. Decoupling the two connectors will cause the fluid pathway of each connector to automatically reseal.

In an aspect, the present disclosure may generally include a self-sealing fluid connector set, comprising a first connector and a second connector. The first connector comprising a first body having a first central cavity that defines a first fluid pathway, a first seal within the first central cavity. The first seal comprising a pair of first interfacing elements positioned adjacent one another at a distal end of the first seal and a first opening configured to remain sealed closed when the first interfacing elements are adjacent, and the first opening opens when the first interfacing elements are separated. The second connector comprising a second body having a second central cavity that defines a second fluid pathway and a second seal within the second central cavity. The second seal comprising a pair of second interfacing elements positioned adjacent one another at a distal end of the second seal and a second opening configured to remain sealed closed when the interfacing elements are adjacent, and the second opening opens when the second interfacing elements are separated. The pair of first interfacing elements aligned perpendicular to pair of second interfacing elements, and the first connector and second connector are configured to fluidly connect by engaging the first interfacing elements and second interfacing elements causing both pairs of first and second interfacing elements to separate causing the opening of first opening and second opening.

Implementations may include one or more of the following features. Each of the first interfacing elements and second interfacing elements is sphere shaped. The second connector may include a pair of clamping members configured to releasable couple to the first connector and the second connector. The pair of clamping members may be attached to an outer surface of the second body and configured to uncouple from the first connector when a proximal end of each of the clamping members pressed toward the second body. The first body may have a pair of notches configured to engage with the pair of clamping members to couple the first connector and second connector together while first opening and second opening remain fluidly sealed. The first connector may include a gasket positioned adjacent an outer surface of the first body and is configured to contact a distal end of the second body when the first connector and second connector are coupled and fluidly connected. A distal end of the first body may include a raised feature and the second body defines a recessed feature along an inner wall of the second central cavity, wherein the raised feature is configured to engage with the recessed feature when the first connector and the second connector are coupled and fluidly connected. The first connector may be configured to receive a first fluid line at the proximal end of the first connector and a sleeve portion of the first seal is configured to seal the connection between first fluid line and the first connector. The second connector may be configured to receive a second fluid line at the proximal end of the second connector and a sleeve portion of the second seal is configured to seal the connection between second fluid line and the second connector. The second connector may include a compression wheel configured to be manually adjusted along a channel defined by the second body, wherein the compression wheel is configured to manually restrict flow of a flow through the second fluid line. The fluid connector set may further include a first spring positioned within the first central cavity to bias the first seal closed. The fluid connector set may further include a second spring within the second central cavity to bias the second seal closed. The shape of the first opening when open and viewed from the distal end of first connector may be generally diamond shaped. The shape of the second opening when open and viewed from the distal end of second connector may be generally diamond shaped.

In another aspect, the present disclosure may generally include a first fluid connector comprising a first body having a first central cavity that defines a first fluid pathway and a first seal within the first central cavity. The first seal comprising a pair of first interfacing elements positioned adjacent one another at a distal end of the first seal and a first opening configured to remain sealed closed when the first interfacing elements are adjacent, and the first opening opens when the first interfacing elements are separated. The first connector may be configured to fluidly connect to a second connector by engaging the first interfacing elements and with a pair of second interfacing elements of the second connector, thereby causing both pairs of first and second interfacing elements to separate causing the opening of first opening and second opening.

In another aspect, the present disclosure may generally include a disposable cassette kit for use with an automated peritoneal dialysis cycler comprising a cassette having a plurality of fluid lines with a plurality of connectors, wherein one connector is disposed at each end of the fluid lines. The connector may comprise a first body having a first central cavity that defines a first fluid pathway and a first seal within the first central cavity. The first seal may comprise a pair of first interfacing elements positioned adjacent one another at a distal end of the first seal and a first opening configured to remain sealed closed when the first interfacing elements are adjacent, and the first opening opens when the first interfacing elements are separated. The first connector may be configured to fluidly connect to a second connector by engaging the first interfacing elements and with a pair of second interfacing elements of the second connector, thereby causing both pairs of first and second interfacing elements to separate causing the opening of first opening and second opening.

Implementations may include the plurality of connectors being color coded to identify the intended use of each fluid line.

In another aspect, the present disclosure may generally include a method of managing fluid line connections as part of a peritoneal dialysis treatment. The method comprising sealing both ends of a drain bag/line to drain connection by decoupling a first fluid connector set, sealing both ends of a solution bag connection by decoupling a second fluid connector set, and sealing both ends of a heater bag connection by decoupling a third fluid connector set. Both ends of each of the first fluid connector set, second fluid connector set, and third fluid connector set may automatically seal upon decoupling.

Implementations may include one or more of the following features. The sealing of both ends of the drain bag/line to drain connection may be simultaneous upon decoupling the first fluid connector set. The sealing of both ends of the solution bag connection may be simultaneous upon decoupling the second fluid connector set. The sealing of both ends of the heater bag connection may be simultaneous upon decoupling the third fluid connector set. Each of the first fluid connector set, second fluid connector set, and third fluid connector set comprises a first connector and a second connector. The first connector comprising a first body having a first central cavity that defines a first fluid pathway; a first seal within the first central cavity. The first seal comprising a pair of first interfacing elements positioned adjacent one another at a distal end of the first seal, and a first opening configured to remain sealed closed when the first interfacing elements are adjacent, and the first opening opens when the first interfacing elements are separated. The second connector comprising a second body having a second central cavity that defines a second fluid pathway, a second seal within the second central cavity. The second seal comprising a pair of second interfacing elements positioned adjacent one another at a distal end of the second seal, a second opening configured to remain sealed closed when the interfacing elements are adjacent, and the second opening opens when the second interfacing elements are separated. The pair of first interfacing elements aligned perpendicular to pair of second interfacing elements and wherein the first connector and second connector are configured to fluidly connect by engaging the first interfacing elements and second interfacing elements causing both pairs of first and second interfacing elements to separate causing the opening of first opening and second opening.

These and other features, aspects, and advantages of the present teachings will become better understood with reference to the following description, examples, and appended claims.

BRIEF DESCRIPTION OF THE DRAWINGS

The foregoing and other objects, features, and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein. In the drawings, like reference numerals generally identify corresponding elements.

DETAILED DESCRIPTION

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

Any documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "about," "approximately," or "substantially" when used in reference to physical characteristics, should be understood to contemplate a range of deviations that would be appreciated by one of ordinary skill in the art to operate satisfactorily for a corresponding use, function, purpose, or the like. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "front," "rear," "top," "bottom," "up," "down," and the like, are words of convenience and are not to be construed as limiting terms unless specifically stated to the contrary.

In general, the connectors, systems, kits, and methods disclosed herein may generally relate to self-sealing fluid connector sets, for example, medical fluid connector sets suitable for use with fluid lines for peritoneal dialysis, hemodialysis, other renal therapies, or other medical therapies. An advantageous use case of the present teachings may be as connector sets for dialysis (i.e., hemodialysis or peritoneal) fluid lines; however, it will be understood that other use cases are contemplated, including without limitation, connector sets for fluid lines both for medical and non-medical application.

Figure 4A:
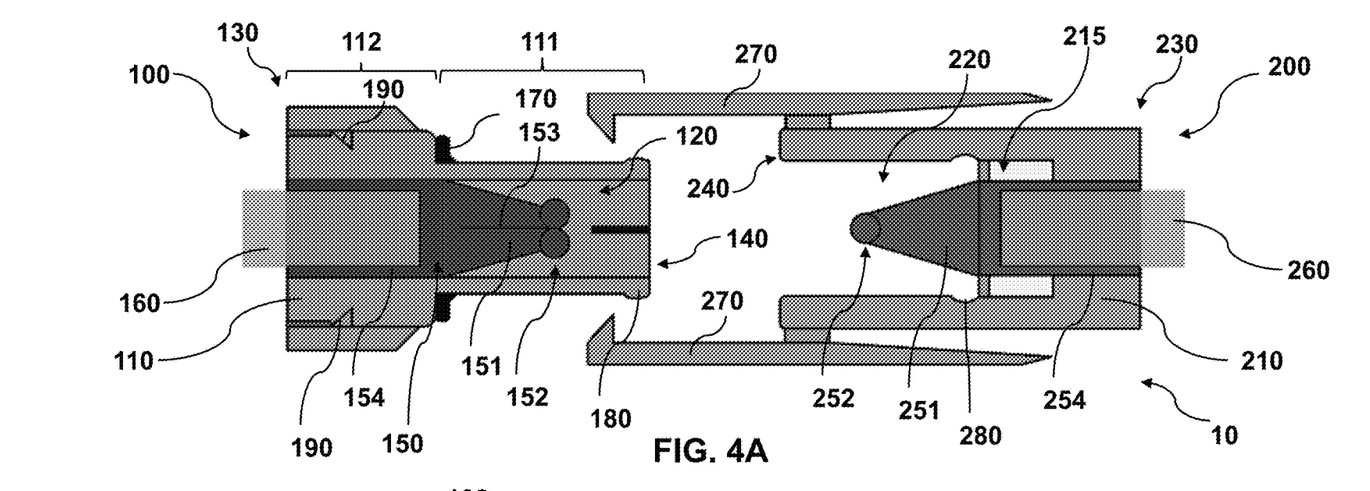
FIG. 4A illustrates a cross sectional schematic of a fluid connector set in a decoupled sealed arrangement, in accordance with a representative embodiment.
Figure 5A:
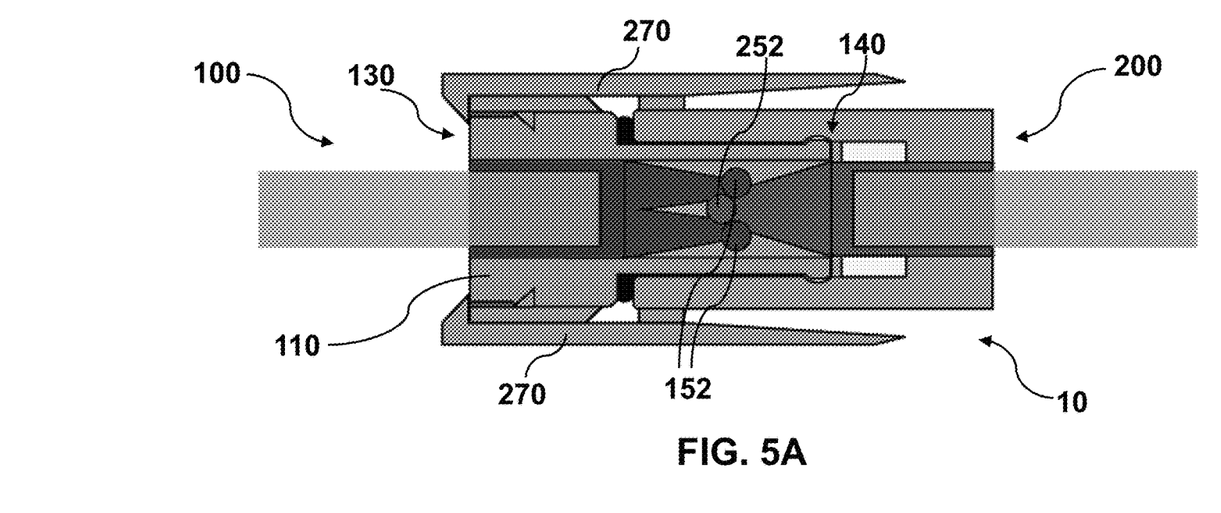
FIG. 5A illustrates a cross sectional schematic of the fluid connector set of FIG. 4A in a coupled and fluidly connected arrangement, in accordance with a representative embodiment.
Figure 6A:
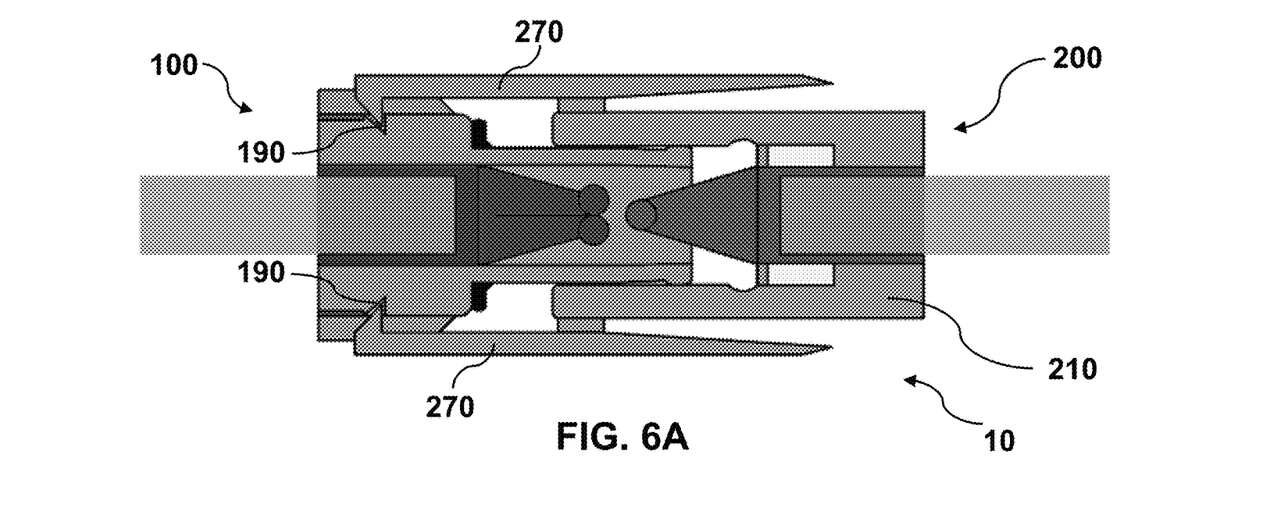
FIG. 6A illustrates a cross sectional schematic of the fluid connector set of FIG. 4A in a coupled and sealed arrangement, in accordance with a representative embodiment.
Figure 6B:
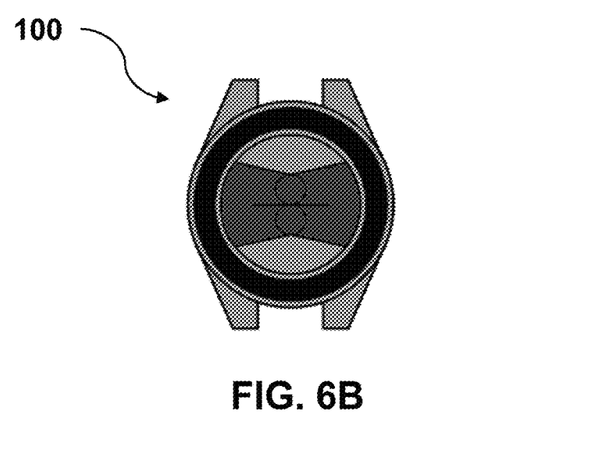
FIG. 6B illustrates a front view of the distal end of the first connector of the fluid connector set of FIG. 6A, in accordance with a representative embodiment.
Figure 6C:
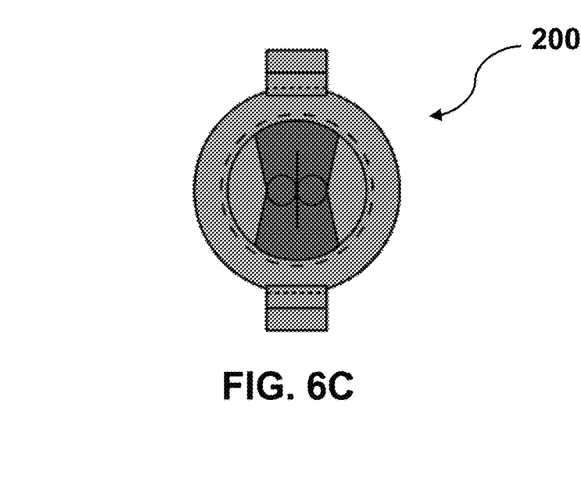
FIG. 6C illustrates a front view of the distal end of the second connector of the fluid connector set of FIG. 6A, in accordance with a representative embodiment.

FIGS. 4A, 5A, and 6A illustrate a cross-sectional view of a self-sealing fluid connector set 10 having a first connector 100 and a second connector 200, in accordance with a representative embodiment. FIG. 4A illustrates first connector 100 and second connector 200 in a decoupled fluidly sealed configuration, FIG. 5A illustrates first connector 100 and second connector 200 in a coupled and fluidly connected configuration, and FIG. 6A illustrates first connector 100 and second connector 200 in a coupled fluidly sealed configuration, in accordance with a representative embodiment. As described herein, fluid connector set 10 may be configured such that a patient or care provider may selectively change the arrangement of fluid connector set 10 (e.g., decoupled fluidly sealed as shown, coupled fluidly connected, coupled fluidly sealed). Thus, it will be understood that first connector 100 and second connector 200 of connector set 10 shown in FIGS. 4A, 5A, and 6A may be the same while being shown in different configurations for understanding of the various features, arrangements, and advantages of fluid connector set 10.

First connector 100 may generally include a first body 110 having a first central cavity 120 that may extend from a proximal end 130 to a distal end 140 of first connector 100. First central cavity 120 may provide at a fluid pathway through first connector 100 between proximal end 130 and distal end 140. First central cavity 120 may be generally cylindrical in shape with a circular cross-section. In some embodiments, first central cavity 120 may have another cross-sectional shape, for example, first central cavity 120 may have a square, oval, or rectangular cross-section. In some embodiments, the cross-section of first central cavity 120 may change at some point along a length of first connector 100 between proximal end 130 and distal end 140.

Figure 4B:
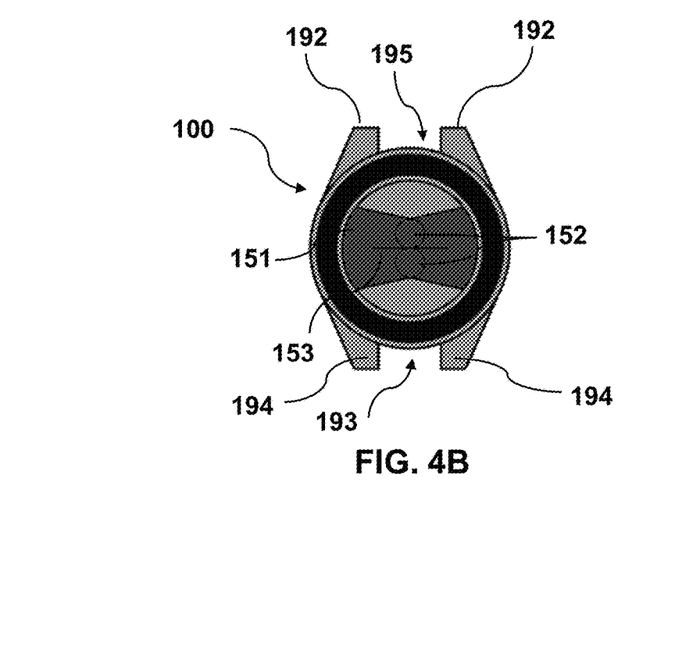
FIG. 4B illustrates a front view of a distal end of a first connector of the fluid connector set of FIG. 4A, in accordance with a representative embodiment.
Figure 5B:
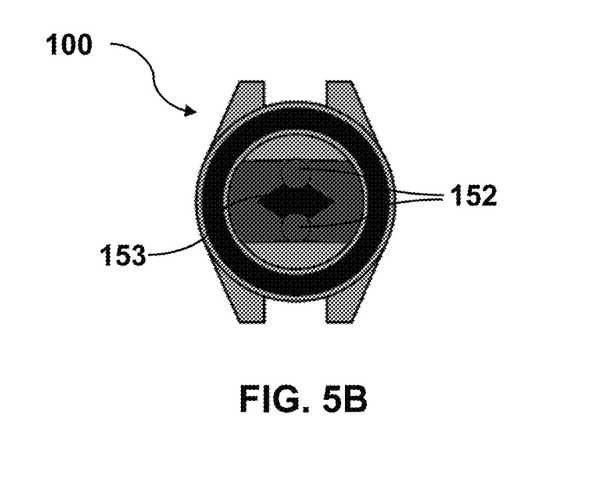
FIG. 5B illustrates a front view of the distal end of the first connector of the fluid connector set of FIG. 5A, in accordance with a representative embodiment.

First connector 100 may have a first seal 150 within first central cavity 120, the position of first seal 150 may be configured to control whether first connector 100 is fluidly sealed or the fluid pathway through first central cavity 120 is open (e.g., when fluidly connected to second connector 200). First seal 150 may include a first narrowing section 151 that extends from an inner wall of first central cavity 120 toward distal end 140. At the distal end of first narrowing section 151, first seal 150 may further include a pair of first interfacing elements 152. First seal 150 may further include a first opening 153 defined by first narrowing section 151 that may extend from between first interfacing elements 152 toward the proximal end of first narrowing section 151. First opening 153 may be configured to be sealed closed (i.e., not preventing fluid passaged) when first interfacing elements 152 are positioned adjacent one another (e.g., as shown in FIGS. 4A and 4B), and first opening 153 opens when the first interfacing elements 152 are separated (e.g., as shown in FIGS. 5A and 5B). First opening 153, when open, may have a generally diamond shape when viewed from the front distal end of first connector 100, as shown in FIG. 5B. In some embodiments, first opening 153 may form another shape when open, for example, first opening may be configured to have a generally square, oval, circular, rectangular, or triangular shape.

First seal 150 may also include a first sleeve section 154 that may extend from first narrowing section 151 toward proximal end 130 along the inner wall of first body 110, as illustrated in FIG. 4A. First connector 100 may be configured to receive a first fluid line 160, and first sleeve section 154 may be configured to fluidly seal the connection between first fluid line 160 and first connector 100. In some embodiments, first seal 150 can be formed of a unitary seal piece, for example, first narrowing section 151, first interfacing element 153, and first sleeve section 154 may all be part of a unitary seal piece. In other embodiments, first seal 151 may be formed of multiple pieces, for example, first sleeve section 154 may be one piece and first narrowing section 151 and first interfacing elements 152 may be formed of a second piece and the two pieces may be positioned adjacent one another in first central cavity 120.

Figure 4C:
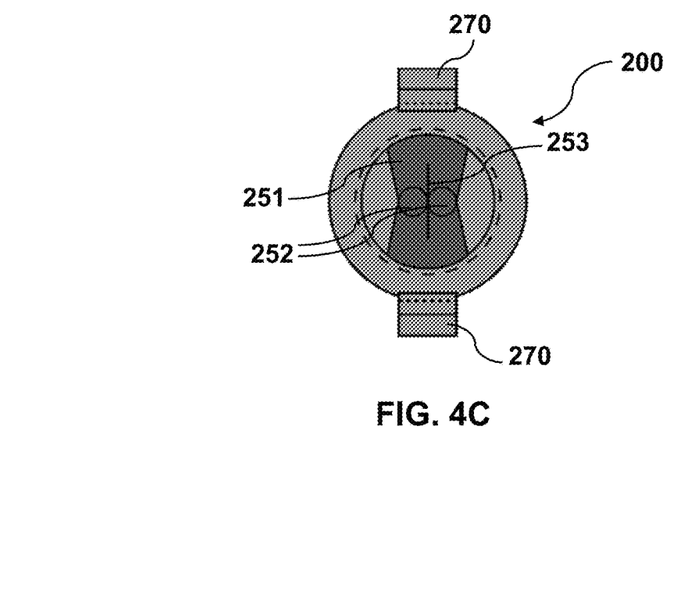
FIG. 4C illustrates a front view of a distal end of a second connector of the fluid connector set of FIG. 4A, in accordance with a representative embodiment.

Referring now to FIGS. 4A and 4C, second connector 200 may generally include a second body 210 having a second central cavity 220 that may extend from a proximal end 230 to a distal end 240 of second connector 200. Second central cavity 120 may provide a fluid pathway through second connector 200 between proximal end 230 and distal end 240. Second central cavity 220 may be generally cylindrical in shape with a circular cross-section. In some embodiments, second central cavity 220 may have another cross-sectional shape, for example, second central cavity 220 may have a square, oval, or rectangular cross-section. In some embodiments, the cross-section of second central cavity 220 may change at some point along a length of second connector 200 between proximal end 230 and distal end 240.

Figure 5C:
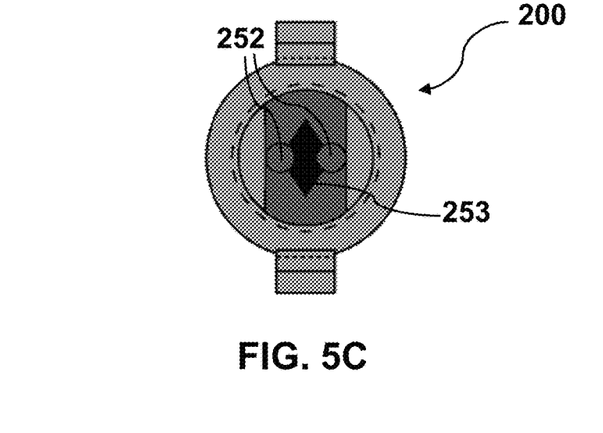
FIG. 5C illustrates a front view of the distal end of the second connector of the fluid connector set of FIG. 5A, in accordance with a representative embodiment.

Second connector 200 may have a second seal 250 within second central cavity 220, the position of second seal 250 may be configured to control whether second connector 200 is fluidly sealed or the fluid pathway through second central cavity 220 is open (e.g., when fluidly connected to first connector 100 as shown in FIG. 5A). Second seal 250 may include a second narrowing section 251 that may extend from an inner wall of second central cavity 220 toward distal end 240. At the distal end of second narrowing section 251, second seal 250 may further include a pair of second interfacing elements 252. Second seal 250 may further include a second opening 253 defined by second narrowing section 251 that may extend from between interfacing elements 252 toward to the proximal end of second narrowing section 251. Second opening 253 may be configured to be sealed closed (i.e., not preventing fluid passaged) when second interfacing elements 252 are positioned adjacent one another (e.g., as shown in FIGS. 4A and 4C), and second opening 253 opens when the second interfacing elements 252 are separated (e.g., as shown in FIGS. 5A and 5C). Second opening 253, when open, may have a generally diamond shape when viewed from the front distal end of second connector 200, as shown in FIG. 5C. In some embodiments, second opening 253 may form another shape when open, for example, second opening may be configured to have a generally square, oval, circular, rectangular, or triangular shape.

Second seal 250 may also include a second sleeve section 254 that may extend from second narrowing section 251 toward proximal end 230 along the inner wall of second body 210, as illustrated in FIG. 4A. Second connector 200 may be configured to receive a second fluid line 260, and second sleeve section 254 may be configured to fluidly seal the connection between second fluid line 260 and second connector 200. In some embodiments, second seal 250 may be formed of a unitary seal piece, for example, second narrowing section 251, second interfacing element 252, and second sleeve section 254 may all be part of a unitary seal piece. In other embodiments, second seal 251 may be formed of multiple pieces, for example, second sleeve section 254 may be one piece and second narrowing section 251 and second interfacing elements 252 may be formed of a second piece and the two pieces may be positioned adjacent one another in second central cavity 220.

In some embodiments, second connector 200 may also include an absorption feature configured to absorb small volumes of fluid that may remain within second central cavity 220 when first connector 100 and second connector 200 are fluidly disconnected by remain clamped (e.g., as shown in FIG. 6A). The absorption feature may be, for example, a hydrophilic ring 215, which may be positioned within second central cavity 220, as shown in FIG. 4A. Hydrophilic ring 215 may be fluidly isolated from the fluid flowing through when first connector 100 and second connector 200 fluidly coupled, as shown in FIG. 5A. In some embodiments, first connector 100 may also be configured to include an absorption feature the same or similar to hydrophilic ring 215.

First body 110 may include an insertion portion 111 and an outer portion 112, as illustrated for example in FIG. 4A. An outer diameter of first body 110 may decrease (e.g., step down or taper) at the transition from outer portion 112 to insertion portion 111. A diameter of insertion portion 11 may be configured to be just less than a diameter of second central cavity 220 at proximal end 240, thereby enabling insertion portion 111 to be inserted within second central cavity 220, as shown in FIG. 5A or FIG. 6A. First connector 100 may also include a gasket 170 that encircles insertion section 111 and positioned adjacent the step-down transition between insertion portion 111 and outer section 112. When first connector 100 and second connector 200 are fully coupled, as shown in FIG. 5A, the distal end of second body 210 may contact and seal against gasket 170, thereby assisting in fluidly sealing the connection between first connector 100 and second connector 200. Although not shown in the figures, in some embodiments, second connector 200 may also have a gasket attached to distal end 240 of second body 210 to further enhance sealing between first connector 100 and second connector 200.

First connector 100 and second connector 200 may also include one or more coupling features configured to secure first connector 100 and second connector 200 when coupled in either a fluidly coupled arrangement (e.g., as shown in FIG. 5A) and/or a coupled (partially) and fluidly sealed arrangement (e.g., as shown in FIG. 6A). For example, insertion portion 111 of first body 110 may include a raised feature 180 configured to engage with a recessed feature 280 along the inner wall of second central cavity 220. In some embodiments, as shown in FIG. 4A, raised feature 180 may be a convex ring and recessed feature 280 can be a corresponding concave ring. Raised feature 180 and recessed feature 280 may be configured to act as a snap-fit type connection. The positioning of raised feature 180 and recessed feature 280 may be such that it can indicate the full insertion of first connector 100 into second connector 200. It is envisioned that in other embodiments, raised feature 180 and recessed feature 280 may be swapped between first connector 100 and second connector 200. For example, second connector 200 may include raised feature 180 while first connector 100 may include recessed feature 280. Additionally, in some embodiments, first connector and second connector may have additional raised and recess features. For example, second connector could have a second recessed ring along the inner wall of second central cavity. This second recessed ring may be positioned to identify partial coupling of first connector and second connector, such that first connector and second connector are coupled but fluidly sealed (e.g., as arranged in FIG. 6A). This may be convenient for a patient to facilitate coupling of the first connector and second connector but keeping them fluidly sealed when desired.

First body 110 and second body 110 may be constructed of a generally rigid medical-grade material, for example, medical grade versions of polyvinyl chloride (PVC), polyethylene, polypropylene, silicone, polyurethane, high density polyethylene, nylon, acrylonitrile butadiene styrene (ABS), acrylic, isoplast, polyisoprene, and polycarbonate.

First seal 150 and second seal 250 may be formed of a flexible material, for example with a durometer such that the material is flexible enough to spread apart with minimal force, but stiff enough to revert to its original closed and sealed position when a separate force is removed. For example, first seal 150 and second seal 250 may be formed of medical grade polyvinyl chloride (PVC), polyethylene, polypropylene, silicone, polyurethane, high density polyethylene, nylon, acrylonitrile butadiene styrene (ABS), acrylic, isoplast, polyisoprene, and polycarbonate.

In some embodiments, although not shown, biasing mechanisms (e.g., springs) may be used to assist with biasing first seal 150 and second seal 250 in the closed sealed position. For example, a first biasing mechanism may be positioned within first central cavity 120 against first narrowing section 151 and/or a second biasing mechanism may be positioned within second central cavity 220 against second narrowing section 152.

First interfacing elements 152 and second interfacing elements 252 may be shaped and positioned relative to one another such that when first connector 100 and second connector 200 are engaged and fully coupled (e.g., as shown in FIG. 5A), first interfacing elements 152 engage with second interfacing elements 252 and cause the simultaneous separation of first interfacing elements 152 and second interfacing elements 252 as shown in FIGS. 5A, 5B, and 5C. Resulting in the opening of first opening 153 and second opening 253 and the fluid coupling of first connector 100/first fluid 160 and second connector 200/second fluid line 260.

In some embodiments, each first interfacing element 152 and each second interfacing element 252 may be generally sphere shaped, as shown in FIGS. 4A, 4B, and 4C. First interfacing elements 152 may be positioned (stacked) on top of one another vertically, when first connector 100 is fluidly sealed, as shown in FIGS. 4A and 4B. Second interfacing elements 252 may be positioned next to one another horizontally, when second connector 200 is fluidly sealed, as shown in FIGS. 4A and 4C. First interfacing elements 152 and second interfacing elements 252 may be positioned perpendicular relative to one another, for example as illustrated in FIGS. 4A, 4B, and 4C. The relative perpendicular positioning enables the rounded surfaces of first interfacing elements 152 and second interfacing elements 252 to contact and slide relative to one another while redirecting the engaging force being applied to first connector 100 and second connector 200 into a separation force on first interfacing elements 152 and second interfacing elements 252, thereby opening first opening 153 and second opening 253. When decoupling first connector 100 and second connector 200, first interfacing elements 152 and second interfacing elements 252 can slide away relative to one another and the inherent bias of first seal 150 and second 250 can cause first interfacing elements 152 to come to together (i.e., return to default position) and second interfacing elements 252 to come together (i.e., return to default position), thereby resulting in the closing of first opening 153 and second opening 253. In other embodiments, the positioning of first interfacing elements 152 and second interfacing element 252 can be swapped while maintaining the perpendicular relative positioning. For example, second interfacing elements 252 may be positioned on top of one another vertically while first interfacing elements 152 may be positioned next to one another horizontally.

In some embodiments, fluid connector set 10 may further include securing mechanism(s) for releasable coupling first connector 100 and second connector 200. For example, as shown in FIGS. 4A, 5A, and 6A, second connector 200 may have a pair of clamping members 270 coupled to an outer surface of second body 210. Clamping members 270 may be configured to extend beyond distal end 240 of second body 210 in order to releasably couple (e.g., clip on) to first body 110. When first connector 100 and second connector 200 are coupled and fluidly connected (e.g., as shown in FIG. 5A), clamping members 270 may extend along first body 110 and clip on to the proximal end 130 of first body 110. Clamping members 270 may also be configured to releasably couple to first body 110 at a position between proximal end 130 and distal end 140, for example, when first connector 100 and second connector 200 are coupled but not fluidly connected (e.g., as shown in FIG. 6A). For example, first body 110 may include a set of notches 190. Notches 190 may be positioned along first body 110 at a distance that results in the coupling of first connector 100 and second connector 200 but short of engaging of first interfacing elements 152 and second interfacing elements 252, thereby resulting in first connector 100 and second connector 200 remaining fluidly sealed.

Decoupling of first connector 100 and second connector 200, whether from the coupled fluidly connected position (e.g., FIG. 5A) or the coupled fluidly sealed position (e.g., FIG. 6A), maybe be accomplished by pressing the proximal ends of clamping members 270 toward second body 210, thereby causing the distal ends of clamping members 270 to move away from first body 110 enabling the retraction of first connector 100 and second connector 200 from on another.

To facilitate alignment of first connector 100 and second connector 200 when coupling, first connector 100 may include alignment features that may extend from the outer surface of first body 110 configure to receive clamping members 270. For example, as shown in FIG. 4B, first connector 100 may include two sets of alignment features 192/194 that extend away from first body 110 on opposite sides and form a pair of channels 193/195 configured to receive clamping members 270. Aligning of clamping members 270 within channels 193/195 when coupling first connector 100 and second connector 200 may deliver proper perpendicular alignment of first interfacing elements 152 and second interfacing elements 252.

It is envisioned that in some embodiments, clamping members 270, notches 190, and alignment features 192/194 may be swapped between first connector 100 and second connector 200. For example, in some embodiments, clamping members 270 may be coupled to the outer surface of first body 110 and second body may include notches 190 and alignment features 192/194.

Figure 2:
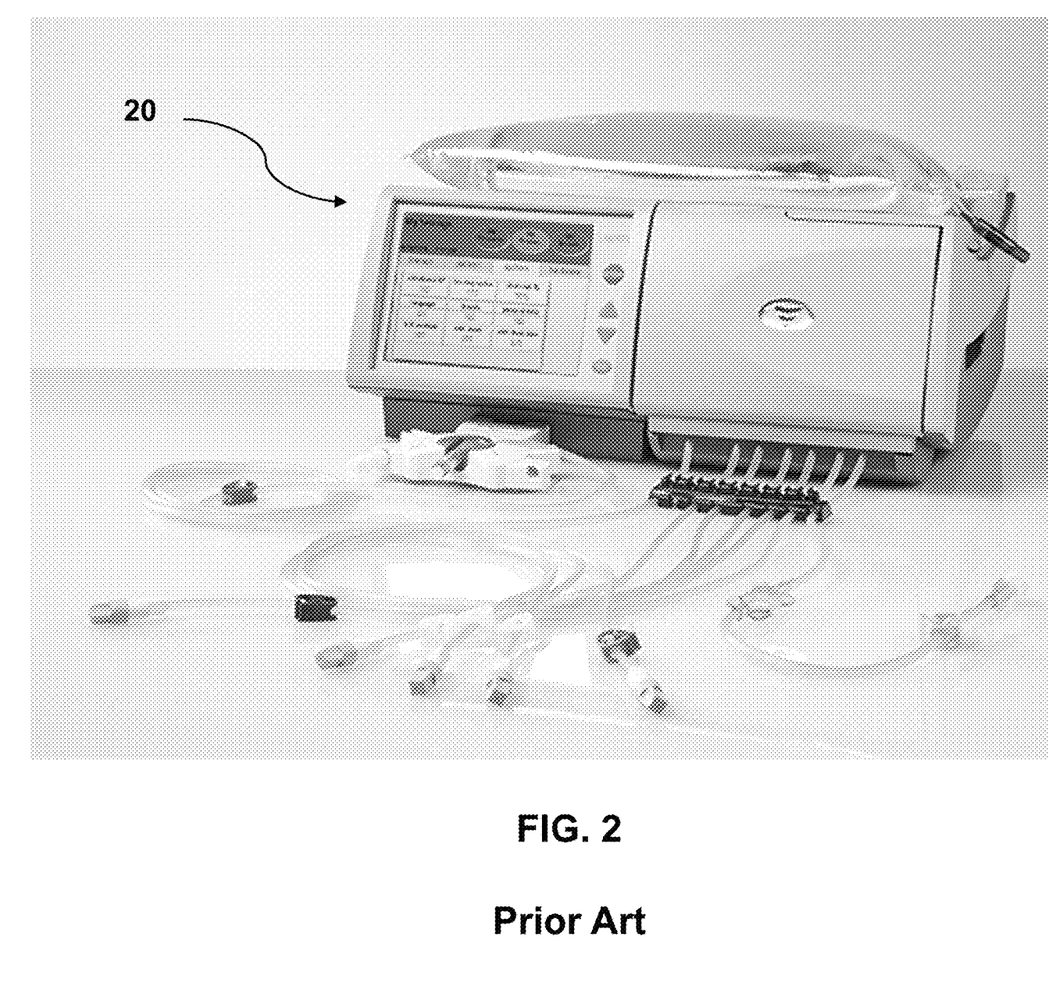
FIG. 2 illustrates an automated peritoneal dialysis (APD) unit.
Figure 7:
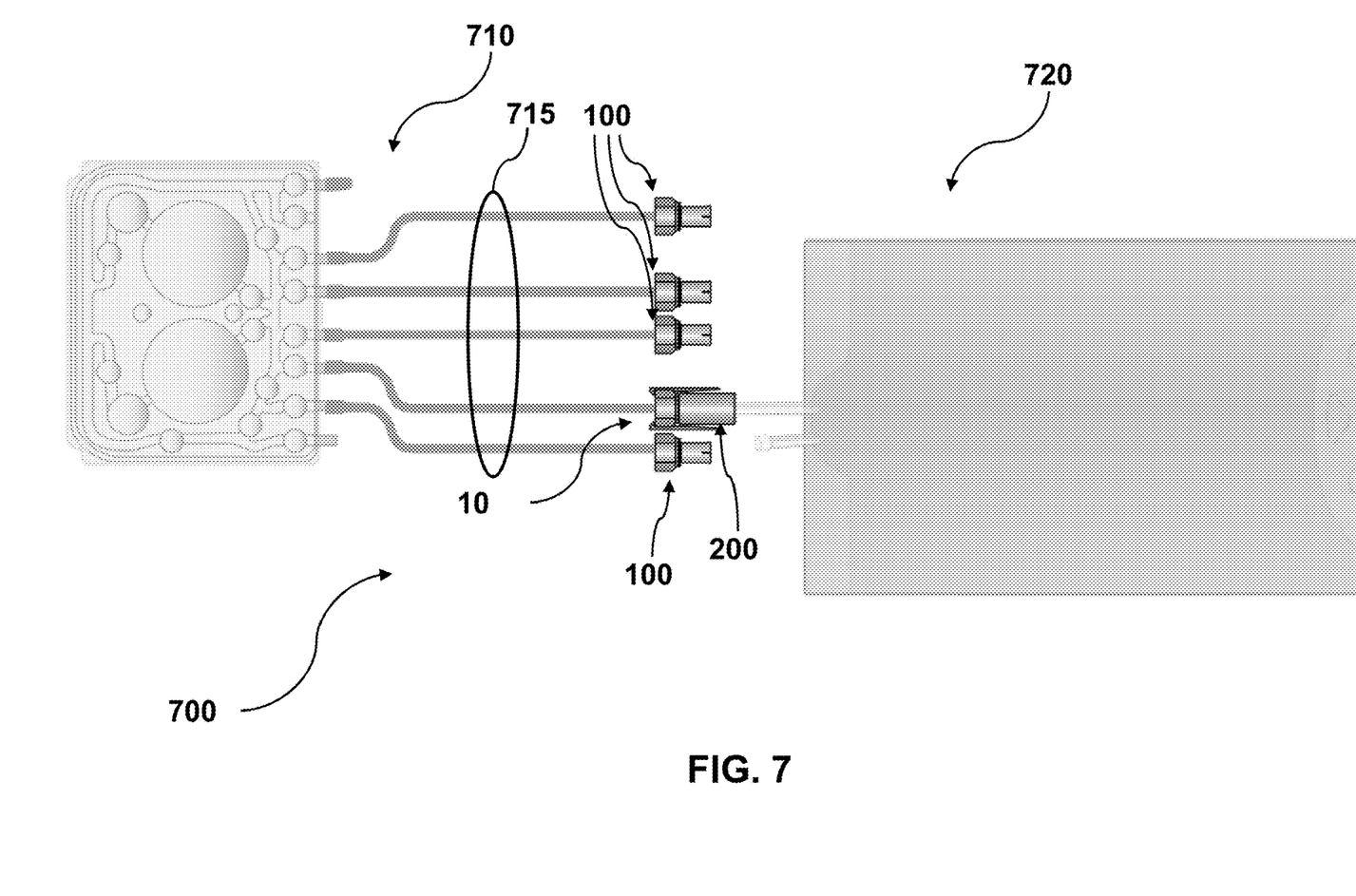
FIG. 7 illustrates as schematic of a kit that may include among other things a fluid connector set fluidly connecting a cassette and a dialysate bag, in accordance with a representative embodiment.

As illustrated in FIG. 7, a fluid connector set 10 may be used to fluidly connect a cassette 710 and a dialysate bag 720. Cassette 710 may have a plurality of fluid lines 715 with a first connector 100 disposed at each end, as shown in FIG. 7. Cassette 710 may be configured for use with an APD cycler (e.g., as illustrated in FIG. 2). A kit 700 may include, among other things, cassette 710, plurality of fluid lines 715, and plurality of first connectors 100. First connectors 100 at each end of fluid lines 715 may enable fluid connection of additional items, for example, a heat bag, additional dialysate bags, a drain bag, a drain line, and/or a patient line. One or more of these additional items may each be configured with a second connector 200 disposed at the connection end to enable coupling and fluid connection to the first connectors 100 disposed at each end of fluid lines 715. In some embodiments, one or more of these additional items may be part of kit 700. It is envisioned, that in some embodiments, first connectors 100 and second connector 200 could be swapped, such that a second connector is disposed at each end of fluid lines 715 while a first connector 100 may be disposed at the connection end of, for example, dialysate bag 720.

In some embodiments, the plurality of first connectors 100 connected to the fluid lines 715 of cassette 710 may be color coded in order to assist the patient with identifying the purpose of fluid lines 715 and making the proper connections. For example, as illustrated in FIG. 2, yellow can identify drain, red can identify heater bag, white can identify solution bags, green can identify last bag, and blue can identify patient line. The same or a similar color coding could be used for first connectors 100 connected to fluid lines 715 and cassette 710, and included as part of kit 700.

Figure 8A:
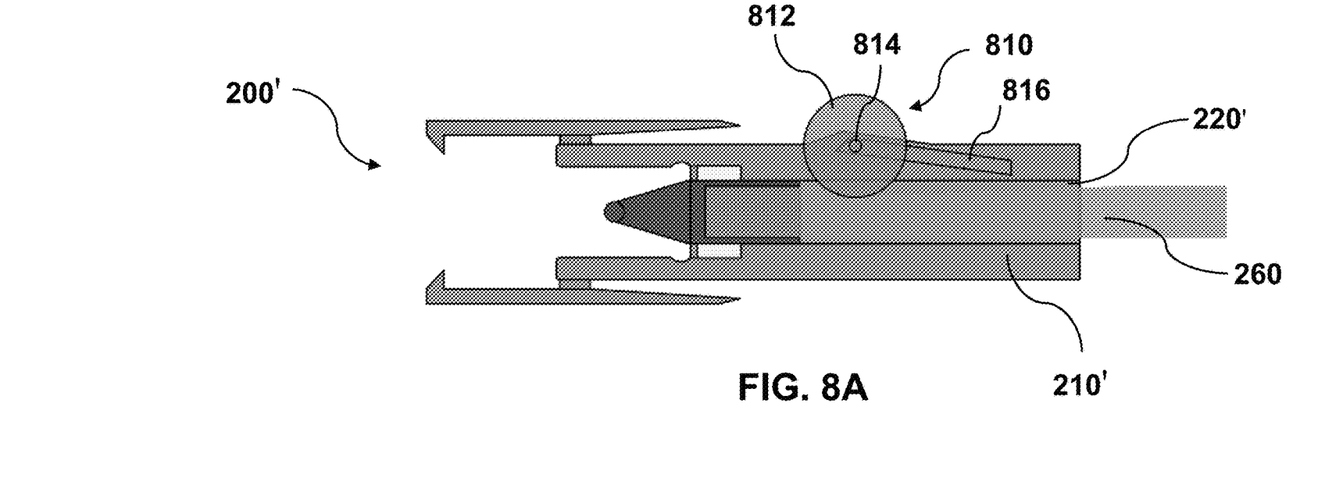
FIG. 8A illustrates a cross sectional schematic of a connector with a flow restriction mechanism, in accordance with a representative embodiment.
Figure 8B:
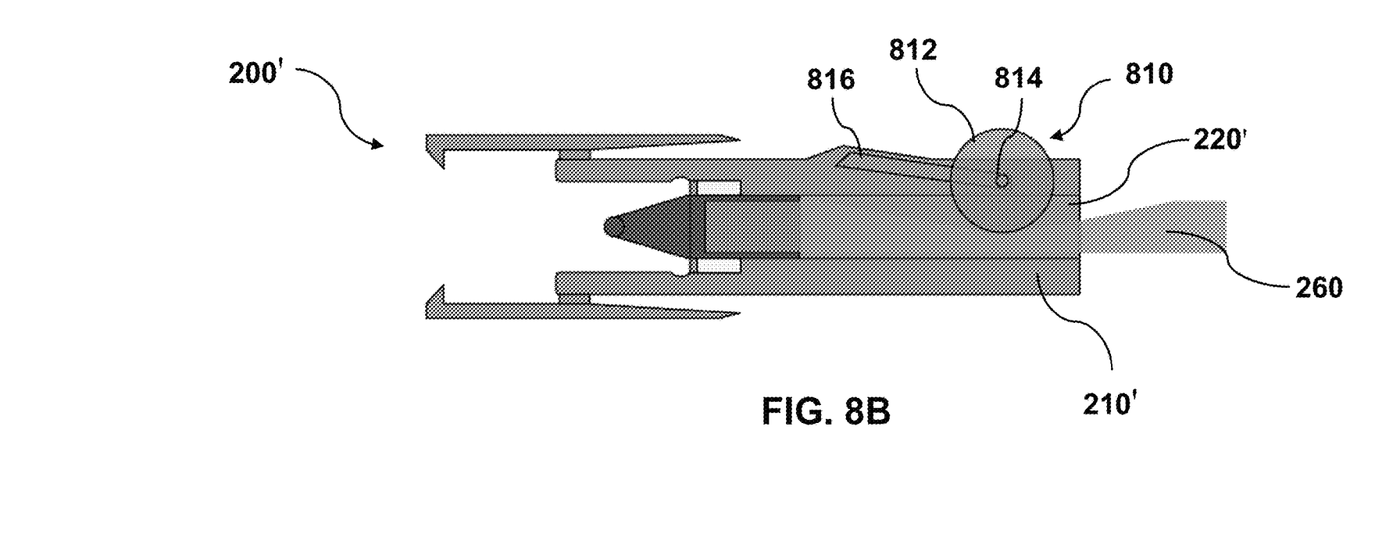
FIG. 8B illustrates a cross sectional schematic of a connector with a flow restriction mechanism, in accordance with a representative embodiment.

In some embodiments, fluid connector set 10 may include an integrated flow restriction mechanism. For example, a second connector 200' as shown in FIGS. 8A and 8B may include a flow restriction mechanism 810. Second connector 200' may be substantially the same as second connector 200, except second connector 200' may have second body 210' that is longer and includes flow restriction mechanism 810, as shown in FIGS. 8A and 8B. Flow restriction mechanism 810 may include a compression wheel 812 with an axial 814 of which is configured to manually slide within a channel 816 that may be defined by second body 210'. Channel 816 may be angled and positioned relative to second central cavity 220' and second fluid line 260, such that when compression wheel 812 and axial 814 are at one end of channel 816 (e.g., distal end as shown in FIG. 8A), wheel 812 may apply minimum (if any) restriction to fluid line 260, and when wheel 812 and axial 814 are at the other end of channel 816 (e.g., proximal end as shown in FIG. 8B), compression wheel 812 may apply maximum restriction to fluid line 260. Restriction to fluid line 260 may be adjusted between minimum and maximum by adjusting the positioning of wheel 812 between the distal and proximal end of channel 816. Maximum restriction to fluid line 260 may equate to different levels of restriction, for example, maximum restriction may mean about 100% or maximum restriction may be less than about 100%, for example, about 90%, about 80%, about 70%, about 60%, or about 50%. Minimum restriction to fluid line 260 may also include different levels of restriction, for example, minimum restriction may mean about 0% restriction or may be more than about 0%, for example, about 10%, about 20%, about 30%, about 40%, or about 50%. Second connector 200' may be advantageous for use on a fluid system that requires manual flow control (e.g., an infusion pump).

It is envisioned that second connector 200' may be fully compatible with first connector 100 and interchangeable with second connector 200 as part of fluid connector set 10, as described herein.

The disclosed fluid connectors and fluid connector sets may be applicable and suitable for both medical and non-medical fluid lines use. The disclosed fluid connectors, fluid connector sets, and kits may be particularly advantageous for use with fluid lines for peritoneal dialysis, hemodialysis, other renal therapies, or other medical therapies. For example, as disclosed herein, an advantageous use case of the fluid connectors sets is for dialysis (i.e., hemodialysis or peritoneal) fluid lines.

Currently, dialysis patients (e.g., PD patients and/or home hemodialysis patients) are typically required to follow instructions that include a series of intricate steps involving clamping, unclamping, connecting and disconnecting lines, which can be a challenge for some patients to complete. The fluid connectors disclosed herein eliminate the need for clamps by providing connectors that fluid pathways open when fluidly coupled (e.g., as shown in FIG. 5A) and fluid pathways self-seal closed when fluidly disconnected (e.g., as shown in FIG. 4A or 6A).

The self-sealing feature of fluid connector set 10 can simplify numerous dialysis treatment steps for dialysis patients. For example, first, traditionally a patient would clamp lines not connected to solution bags. By utilizing connector sets 10, this would no longer be required because first connector 100 or second connector 200 at the end of each line would stay closed when not fluidly coupled. Second, traditionally a patient would clamp the drain bag/line to drain when disconnecting. By utilizing connector sets 10 for the drain bag/line connection, simply decoupling connector set 10 would fluidly seal first connector 100 and second connector 200 connected to either end of the connection. Third, traditionally a patient would clamp each of the lines (e.g., drain line, four solution bag lines, heater bag line, and patient line) of a cassette when disposing of it. By utilizing connector set 10, simply decoupling all the cassette lines would fluidly seal first connector 100 connected to each end of the cassette lines. Lastly, traditionally a patient would clamp solution supply bags when disposing of them. By utilizing connector set 10, simply decoupling of the solution supply bags would fluidly seal, for example, second connector 200 connected to the end of each solution supply bag line.

Figure 9:
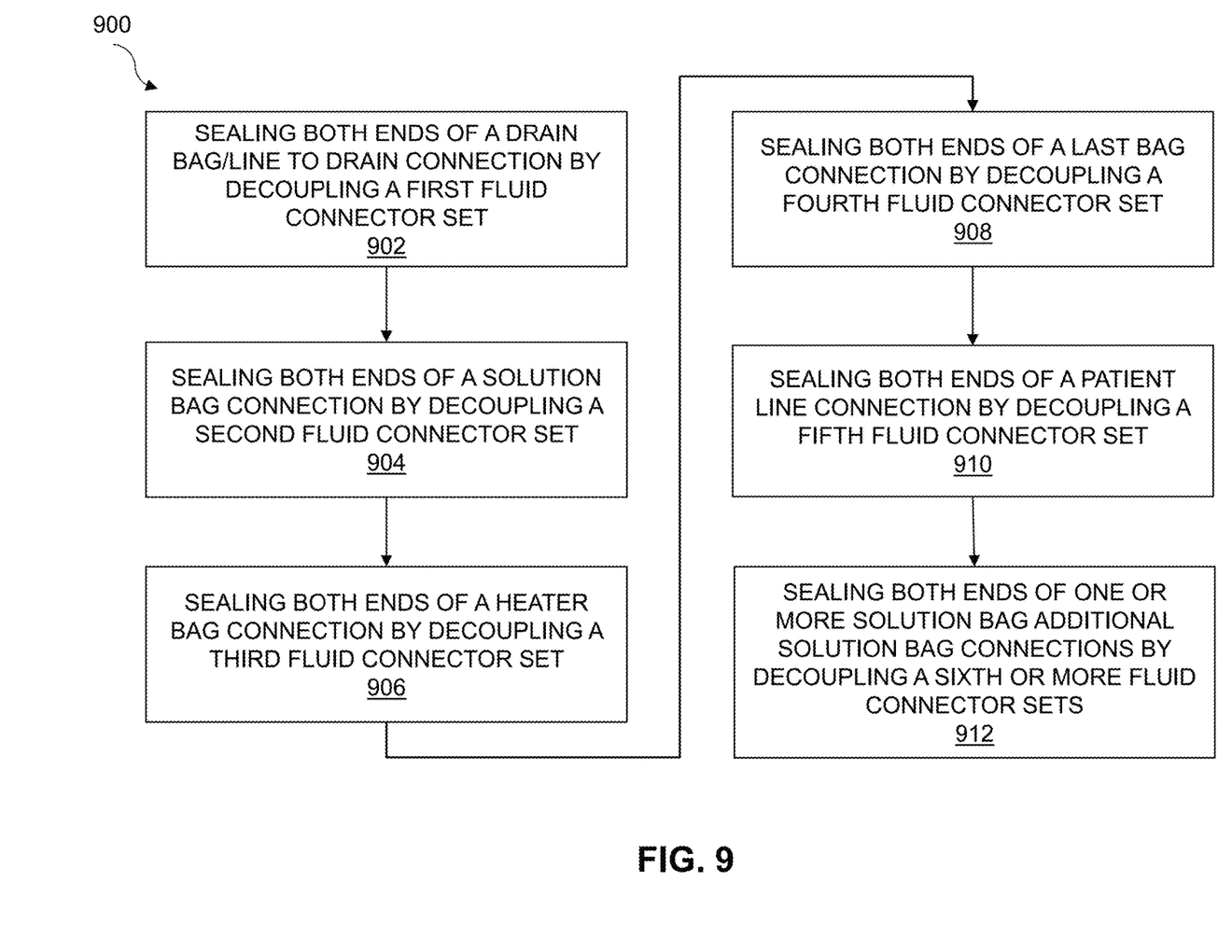
FIG. 9 is a flow chart of a method for managing fluid line connections as part of a peritoneal dialysis treatment, in accordance with a representative embodiment.

FIG. 9 is a flow chart of a method of managing fluid line connections as part of a peritoneal dialysis treatment, in accordance with a representative embodiment. The method 900 may be performed using any of the fluid connector sets, fluid connectors, and kits described herein. Thus, any of the components recited in the method 900 will be understood as potentially including any of the corresponding components described herein, e.g., with reference to the other figures.

As shown in step 902, the method 900 may include sealing both ends of a drain bag/line to drain connection by decoupling a first fluid connector set. As shown in step 904, the method 900 may include sealing both ends of a solution bag connection by decoupling a second fluid connector set. As shown in step 906, the method 900 may include sealing both ends of a heater bag connection by decoupling a third fluid connector set. As shown in step 908, the method 900 may optionally include sealing both ends of a last bag connection by decoupling a fourth fluid connector set. As shown in step 910, the method 900 may optionally include sealing both ends of a patient line connection by decoupling a fifth fluid connector set. As shown in step 912, the method 900 may optionally include sealing both ends of one or more additional solution bag connections by decoupling a sixth or more fluid connector sets. The sealing of both ends of a fluid connector set (e.g., first, second, third, fourth, fifth, or sixth fluid connector set) may be simultaneous upon decoupling of that fluid connector set.

Additional advantages of the disclosed fluid connectors include simplified manufacturing assembly and reduction in medical waste. For example, less complex assembly is needed when attaching the disclosed fluid connectors to lines compared to the threading of fluid lines through traditional clamps (e.g., as shown in FIGS. 2 and 3) and then attaching a connector (e.g., Luer connector) to the end. The sheer number of disposable clamps needed per treatment contributes both to cost and medical waste. Eliminating the need for these clamps can reduce both costs per treatment and waste while at the same time simplifying treatment sets for patients.

The foregoing description, for purpose of explanation, has been described with reference to specific embodiments. However, the illustrative discussions above are not intended to be exhaustive or to limit the disclosure to the precise forms disclosed. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

Unless the context clearly requires otherwise, throughout the description, the words "comprise," "comprising," "include," "including," and the like are to be construed in an inclusive sense as opposed to an exclusive or exhaustive sense; that is to say, in a sense of "including, but not limited to." Additionally, the words "herein," "hereunder," "above," "below," and words of similar import refer to this application as a whole and not to any particular portions of this application.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity and need not be located within a particular jurisdiction.

What is claimed is:

1. A self-sealing fluid connector set, comprising:
a first connector and a second connector;
the first connector comprising:
a first body having a first central cavity that defines a first fluid pathway;
a first seal within the first central cavity, the first seal comprising:
a pair of first interfacing elements positioned adjacent one another at a distal end of the first seal; and
a first opening configured to remain sealed closed when the first interfacing elements are adjacent one another, and the first opening configured to open when the first interfacing elements are separated;
the second connector comprising:
a second body having a second central cavity that defines a second fluid pathway;
a second seal within the second central cavity, the second seal comprising:
a pair of second interfacing elements positioned adjacent one another at a distal end of the second seal;
a second opening configured to remain sealed closed when the interfacing elements are adjacent one another, and the second opening configured to open when the second interfacing elements are separated;
wherein the pair of first interfacing elements aligned perpendicular to the pair of second interfacing elements; and
wherein the first connector and second connector are configured to fluidly connect by engaging the first interfacing elements and second interfacing elements causing both pairs of first and second interfacing elements to separate causing the opening of first opening and second opening.

2. The self-sealing sealing fluid connector set of claim 1, wherein each of the first interfacing elements and second interfacing elements is sphere shaped.

3. The self-sealing sealing fluid connector set of claim 1, wherein the second connector includes a pair of clamping members configured to releasable couple to the first connector and the second connector.

4. The self-sealing sealing fluid connector set of claim 3, wherein the pair of clamping members are attached to an outer surface of the second body and configured to uncouple from the first connector when a proximal end of each of the clamping members pressed toward the second body.

5. The self-sealing sealing fluid connector set of claim 3, wherein the first body has a pair of notches configured to engage with the pair of clamping members to couple the first connector and second connector together while first opening and second opening remain fluidly sealed.

6. The self-sealing sealing fluid connector set of claim 1, wherein the first connector includes a gasket positioned adjacent an outer surface of the first body and is configured to contact a distal end of the second body when the first connector and second connector are coupled and fluidly connected.

7. The self-sealing sealing fluid connector set of claim 1, wherein:
a distal end of the first body includes a raised feature; and
the second body defines a recessed feature along an inner wall of the second central cavity;
wherein the raised feature is configured to engage with the recessed feature when the first connector and the second connector are coupled and fluidly connected.

8. The self-sealing sealing fluid connector set of claim 1, wherein the first connector is configured to receive a first fluid line at the proximal end of the first connector and a sleeve portion of the first seal is configured to seal the connection between first fluid line and the first connector.

9. The self-sealing sealing fluid connector set of claim 1, wherein the second connector is configured to receive a second fluid line at the proximal end of the second connector and a sleeve portion of the second seal is configured to seal the connection between second fluid line and the second connector.

10. The self-sealing sealing fluid connector set of claim 9, wherein the second connector includes a compression wheel configured to be manually adjusted along a channel defined by the second body, wherein the compression wheel is configured to manually restrict flow of a flow through the second fluid line.

11. The self-sealing sealing fluid connector set of claim 1, further comprising a first spring positioned within the first central cavity to bias the first seal closed.

12. The self-sealing sealing fluid connector set of claim 1, further comprising a second spring positioned within the second central cavity to bias the second seal closed.

13. The self-sealing sealing fluid connector set of claim 1, wherein the shape of the first opening when open and viewed from the distal end of first connector is generally diamond shaped.

14. The self-sealing sealing fluid connector set of claim 1, wherein the shape of the second opening when open and viewed from the distal end of second connector is generally diamond shaped.

* * * * *